(12) United States Patent
Wang et al.

(10) Patent No.: US 9,034,172 B2
(45) Date of Patent: May 19, 2015

(54) ELECTROCHEMICAL TEST SENSOR

(75) Inventors: Yuan Wang, Mountain lakes, NJ (US); Raeann Gifford, Cortland Manor, NY (US); Hualin Jiang, Granger, IN (US); Jeffery S. Reynolds, New Fairfield, CT (US); Jianfeng Fei, Sleepy Hollow, NY (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 483 days.

(21) Appl. No.: 12/877,207

(22) Filed: Sep. 8, 2010

(65) Prior Publication Data
US 2011/0056848 A1 Mar. 10, 2011

Related U.S. Application Data

(60) Provisional application No. 61/240,619, filed on Sep. 8, 2009.

(51) Int. Cl.
G01N 27/30 (2006.01)
G01N 33/50 (2006.01)
G01N 27/327 (2006.01)

(52) U.S. Cl.
CPC .................................. *G01N 27/3272* (2013.01)

(58) Field of Classification Search
CPC ................................................... G01N 27/3272
USPC ................... 205/792; 600/435, 437
See application file for complete search history.

(56) References Cited

U.S. PATENT DOCUMENTS

| | | | | |
|---|---|---|---|---|
| 5,390,671 A | * | 2/1995 | Lord et al. | 600/347 |
| 5,586,553 A | * | 12/1996 | Halili et al. | 600/316 |
| 2002/0103499 A1 | | 8/2002 | Perez et al. | |
| 2004/0094432 A1 | * | 5/2004 | Neel et al. | 205/777.5 |
| 2005/0232813 A1 | | 10/2005 | Karmali | |

(Continued)

FOREIGN PATENT DOCUMENTS

| | | | | |
|---|---|---|---|---|
| EP | 0351892 A2 | 1/1990 | | G01N 27/28 |
| EP | 1285629 A1 | 2/2003 | | A61B 5/15 |
| EP | 1402812 A1 | 3/2004 | | A61B 5/00 |

(Continued)

OTHER PUBLICATIONS

Cadence Science Needles pamphlet.*

(Continued)

*Primary Examiner* — Luan Van
*Assistant Examiner* — Steven Rosenwald
(74) *Attorney, Agent, or Firm* — Nixon Peabody LLP

(57) ABSTRACT

An electrochemical test sensor for detecting the concentration of an analyte in a fluid sample. The electrochemical test sensor includes a housing that has a first end and a second opposing end. The housing includes an opening at the first end to receive a fluid test sample. An electrode assembly includes a substrate, a working electrode, a counter electrode and a reagent. The substrate has a first surface and an opposing second surface. The working electrode is disposed on the first surface of the substrate, and the counter electrode is disposed on the second surface of the substrate. The electrode assembly is positioned within the housing to define a reaction channel. The electrochemical test sensor may be used with a removable lancet mechanism or integrated within a lancet mechanism to form one integral unit.

24 Claims, 4 Drawing Sheets

(56) References Cited

U.S. PATENT DOCUMENTS

2006/0178573 A1* 8/2006 Kermani et al. ............. 600/347
2009/0156920 A1* 6/2009 Kotzan et al. ................ 600/347

FOREIGN PATENT DOCUMENTS

JP           6-109688         4/1994   ............. G01N 27/28
WO     WO 96/00614 A1        1/1996   ................ B01L 3/02

OTHER PUBLICATIONS

International Written Opinion, mailed Jul. 12, 2010, which issued during prosecution of corresponding International Patent Application No. PCT/US2010/048120 (6 pages).

International Search Report, mailed Jul. 12, 2010, which issued during prosecution of corresponding International Patent Application No. PCT/US2010/048120 (5 pages).

* cited by examiner

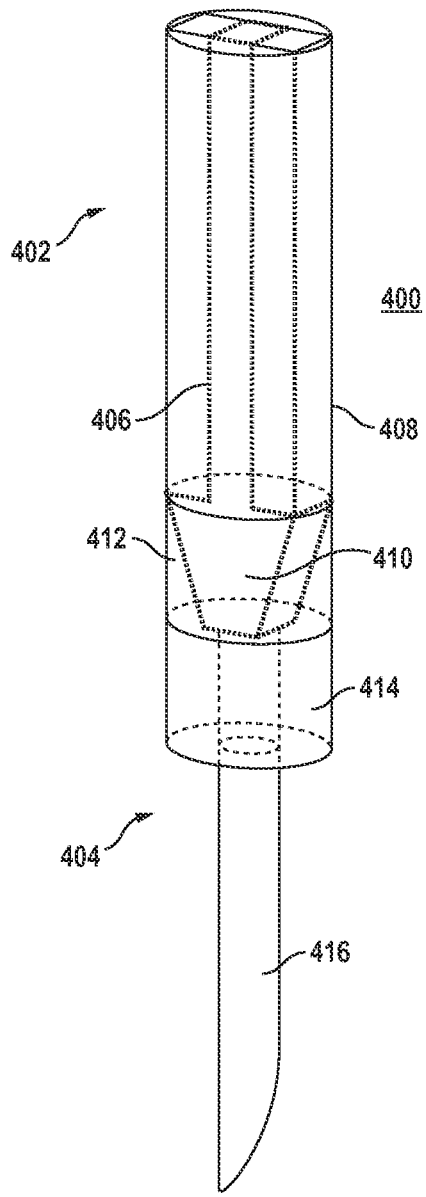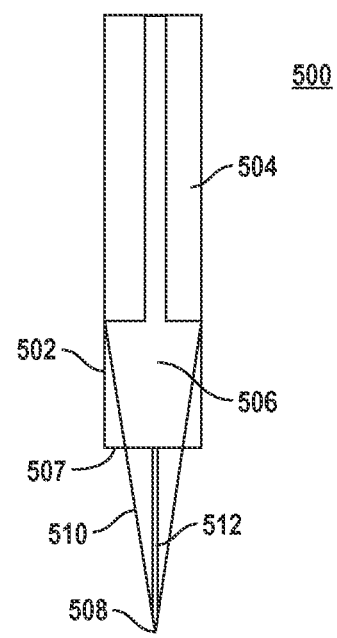
FIG. 5
FIG. 6

ELECTROCHEMICAL TEST SENSOR

REFERENCE TO RELATED APPLICATIONS

This application claims priority to U.S. Provisional Patent Application Ser. No. 61/240,619, filed Sep. 8, 2009, and entitled "Electrochemical Test Sensor," which is incorporated herein in its entirety.

TECHNICAL FIELD

The present disclosure relates generally to test sensors, and more specifically to an electrochemical test sensor that is adapted to determine the concentration of an analyte.

BACKGROUND

Medical conditions such as diabetes require a person afflicted with the condition to regularly self-monitor that person's blood-glucose concentration level. The purpose of monitoring the blood glucose concentration level is to determine the person's blood glucose concentration level and then to take corrective action, based upon whether the level is too high or too low, to bring the level back within a normal range. The failure to take corrective action may have serious medical implications for that person.

One method of monitoring a person's blood glucose level is with a portable testing device. The portable nature of these devices enables users to conveniently test their blood glucose levels at different locations. One type of device utilizes an electrochemical test sensor to harvest and analyze the blood sample. The test sensor typically includes a capillary channel to receive the blood sample and a plurality of electrodes. Some electrochemical test sensor devices have larger capillary channels than are optimally desired. The bigger the capillary channel, the more blood from a person is required to fill the channel. Because drawing blood from a person is unpleasant, it would also be desirable to reduce the size of the capillary channel to require less blood. However, there must be sufficient blood to cover and activate the plurality of electrodes used in an electrochemical test sensor. Thus, there exists a need for an electrochemical test sensor with a smaller capillary channel without sacrificing the accuracy of the analyte concentration determination.

BRIEF DESCRIPTION OF THE DRAWINGS

FIG. 5 is a perspective view of an electrochemical test sensor with a lancet mechanism according to an embodiment.

FIG. 6 is a perspective view of an electrochemical test sensor with an integrated lancet mechanism according to an embodiment.

DESCRIPTION OF ILLUSTRATED EMBODIMENTS

The present invention is directed to an electrochemical test sensor that is adapted to be placed into a meter or an instrument and assist in determining an analyte concentration in a body fluid sample. The present electrochemical sensor assists in reducing the volume of the fluid sample needed to properly determine the analyte concentration. The body fluid sample may be collected with a lancing device with which the electrochemical sensor is coupled thereto or integrated therewith.

Examples of the types of analytes that may be collected include glucose, lipid profiles (e.g., cholesterol, triglycerides, LDL and HDL), microalbumin, hemoglobin $Al_C$, fructose, lactate, or bilirubin. It is contemplated that other analyte concentrations may also be determined. It is also contemplated that more than one analyte may be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

Figure 1A:
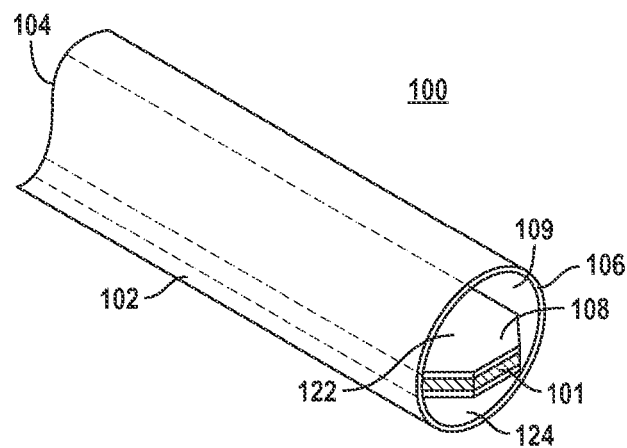
FIG. 1A is a perspective view of an electrochemical test sensor according to an embodiment.
Figure 1B:
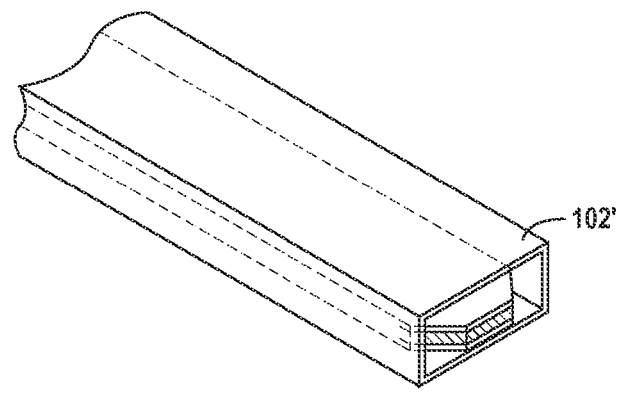
FIG. 1B is a perspective view of an electrochemical test sensor according to another embodiment.

FIG. 1A illustrates a perspective view of an electrochemical test sensor in accordance with an embodiment. FIG. 1B is a perspective view of an electrochemical test sensor according to another embodiment. As shown in FIG. 1A, an electrochemical test sensor 100 includes a housing 102 having a meter-contact end 104, a front opening end 106, and an electrode assembly 108 positioned within the housing 102. As shown in FIGS. 1A and 1B, the housing 102 is generally cylindrical in shape, whereby at least a portion of the housing 102 (desirably at the front opening end) may have a cross-sectional shape such as circular (FIG. 1A). The housing may have a rectangular cross-sectional shape such as shown with housing 102' (FIG. 1B). It is contemplated that the housing may have other polygonal or non-polygonal cross-sectional shapes.

Figure 2A:
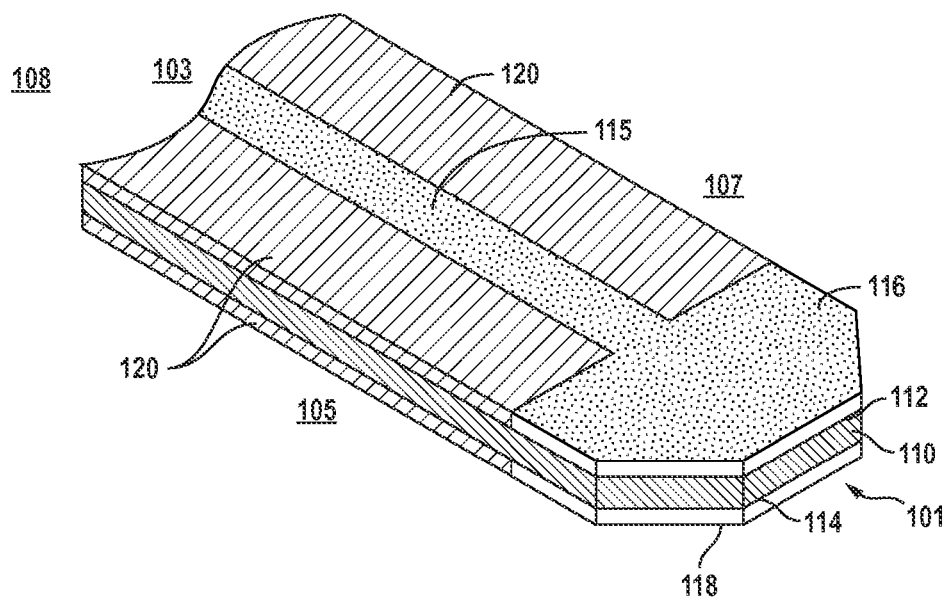
FIG. 2A is a perspective view of an electrode assembly according to an embodiment.
Figure 2B:
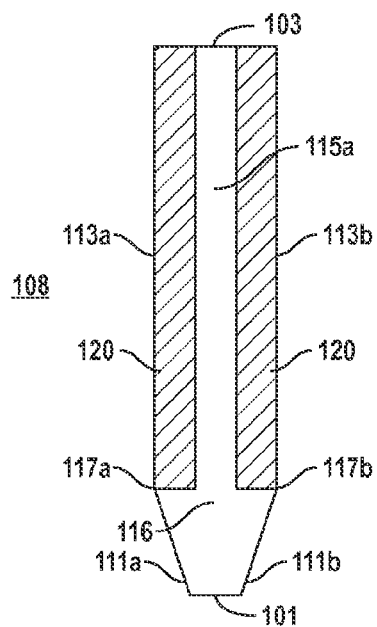
FIG. 2B is a top view of the electrode assembly of FIG. 2A.
Figure 2C:
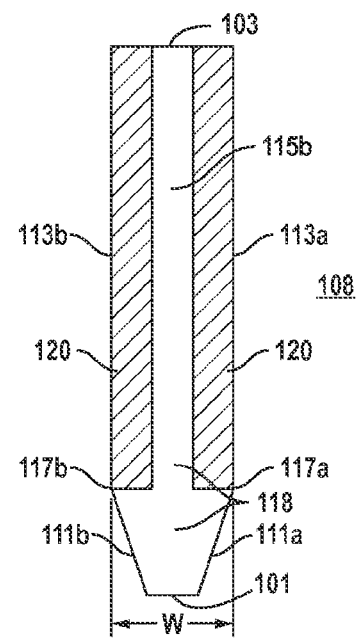
FIG. 2C is a bottom view of the electrode assembly of FIG. 2A.
Figure 2D:
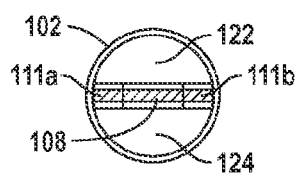
FIG. 2D is a front view of electrochemical test sensor of FIG. 1A.

The electrode assembly 108 is shown in FIGS. 1A and 1B within the interior of the housing 102, whereby at least a portion of the assembly 108 is configured to separate the interior of the housing into distinct capillary channels 122, 124 (see also FIG. 2D). A reaction channel 109 (FIG. 1A) is shown as the volume within the housing 102 that surrounds the tip (described below) of the electrode assembly's front end 101 (FIG. 2A). In an embodiment, the front end 101 of the electrode assembly 108 is located inward a set distance from the front opening end 106 such that the reaction channel 109 occupies the space between the front opening end 106 and the front end 101 of the electrode assembly 108. It is contemplated that the front end of the electrode assembly may be positioned differently with respect to the front opening end of the reaction channel. For example, a front end of the electrode assembly may be flush with the front opening end of the housing. In another example, a front end of the electrode assembly may extend outwardly from the front opening end and, thus, would be exposed outside the housing. In a further example, the length of the housing 102 may be smaller than depicted in FIG. 1a as long the length of the housing is sufficient to allow the sample to travel from the sensor tip. In operation, the user's fluid sample is received within the reaction channel 109 wherein analyte in the fluid sample reacts with the electrodes of the electrode assembly and is then used to determine analyte concentration in the sample.

FIG. 2A illustrates a perspective view of the electrode assembly in accordance with an embodiment. FIGS. 2B and 2C show respective top and bottom views of the electrode assembly shown in FIG. 2A. As shown in FIG. 2A, the electrode assembly 108 includes a substrate 110 having a first surface 112 and a second surface 114, a working electrode 116 and a counter electrode 118. The working electrode 116 is disposed on the first surface 112 and the counter electrode 118 is disposed on the second surface 114. The working electrode 116 and counter electrode 118 are thus disposed on opposing surfaces of the substrate and are effectively in a back-to-back configuration with respect to the substrate 110. This is further shown in FIG. 2B in which the working electrode 116 is shown exposed when viewing the assembly 108 from one side, whereas the counter electrode 118 is shown exposed when the electrode assembly 108 is flipped onto the opposing side (see FIG. 2C).

As shown in FIG. 2C, the electrode assembly 108 desirably has a uniform width dimension W along a substantial portion of its length, however this is not necessary. In this embodiment, the width dimension W is substantially equal to the inside diameter or width dimension of the housing 102. By having such a width dimension, the electrode assembly 108 affectively separates the interior of the housing into a first capillary channel 122 and a second capillary channel 124 in FIG. 2D, except desirably proximal to the tip. The back-to-back configuration of the working and counter electrodes 116, 118 is advantageous in this embodiment, because the electrodes 116, 118 may effectively operate while minimizing the amount of required capillary space to perform the analysis on the fluid sample. This, in turn, allows the electrode assembly 108 to effectively perform the analysis on a smaller amount of fluid sample.

Figure 2E:
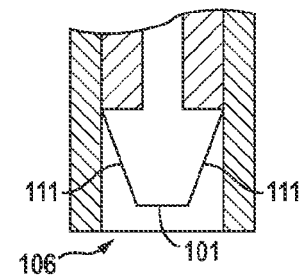
FIG. 2E is a top view of the reaction channel of an electrochemical test sensor of FIG. 1A.

As shown in FIGS. 2B and 2C, the electrode assembly 108 has two sides 113a, 113b and also two tapering sides 111a, 111b between points 117a, 117b and the front end 101. This entire front portion of the electrode assembly 108 between points 117a, 117b and the front end 101 is generally referred to as the tip of the electrode assembly 108. As shown in FIGS. 2A-2C, the front end 101 is a relatively straight edge, although this is not necessary. As stated above, the reaction channel 109 is the volume within the housing 102 that surrounds the tip of the electrode assembly 108. The sides 111a, 111b of the electrode assembly 108 desirably abut in inside surface of the tube 102, as shown in FIG. 2D. This configuration creates a working area that links or allows fluid communication between the two capillary channels 122, 124 near the front opening 106 of the housing as shown in FIG. 2E. This configuration assists in increasing capillary action of the fluid as it is received by the sensor.

It is contemplated that the front end may alternatively be a pointed end, a rounded edge or other shapes. It should be noted that it is not required that both sides 111a, 111b of the electrode assembly 108 taper toward one another. It is contemplated that only one side may be straight while the other opposing side is configured at an angle. In another embodiment, the tip may have other appropriate shapes such as semicircular, bow-tie, and the like that desirably increase capillary action of the fluid received between the two channels.

The working electrode 116 and the counter electrode 118 assist in electrochemically determining the analyte concentration of the received fluid sample. In one embodiment, the working electrode 116 and the counter electrode 118 may be made from conductive material including, but not limited to, carbon, gold, platinum, ruthenium, rhodium, palladium or combinations thereof. The electrodes typically connect with the meter contact area using an electrode pattern. The electrode pattern may include test-sensor contact and conductive leads. The working electrode area is less than 1.0 mm$^2$ and desirably about 0.5 or 0.6 mm$^2$ or even 0.3 mm$^2$. The electrodes may be formed by techniques such as screen printing, sputtering, laser ablation, combinations thereof or other manufacturing methods.

The substrate may be made of polymeric materials including but not limited to polyethylene terephthalate (PET), polysterene, polyimide, polycarbonate and combinations thereof. The housing 102 may be made of polymeric materials such as polyvinyl chloride (PVC) and the like. The housing may be made of metallic materials and alloys such as, for example, nickel-titanium alloy or nitinol. Nitinol may be desirable because of its shape memory and superelasticity. The interior of the housing may include a hydrophilic coating to increase the fill rate of the liquid sample into the capillary channels.

A reagent is desirably disposed on the working electrode 116 in FIG. 2B. A reagent may additionally or alternatively be disposed on the counter electrode 118 in FIG. 2C. In particular, the reagent is located along a portion of or the entire surfaces of one or more of the electrodes 116, 118. The reagent converts an analyte (e.g., glucose) in the fluid test sample, stoichiometrically into a chemical species that is electrochemically measurable, in terms of electrical current it produces, by the components of the working electrode 116 and the counter electrode 118. The reagent typically includes an enzyme and an electron acceptor. The enzyme reacts with the analyte to produce mobile electrons on the working and counter electrodes 116, 118. For example, the reagent layer may include glucose oxidase, glucose dehydrogenase (GDH), and/or a surfactant if the analyte to be determined is glucose. The enzyme in the reagent layer may be combined with a hydrophilic polymer such as poly(ethylene oxide) or other polymers such as polyethylene oxide (PEO), hydroxyethyl cellulose (HEC), carboxymethylcellulose (CMC) and polyvinyl acetate (PVA). The electron acceptor (e.g., ferricyanide salt) carries the mobile electrons to the surface of the working electrode 116. Amperometry detection methods and gated amperometry detection methods may be applied to analyze the sample. Other diffusional electron mediators, such as ferrocene derivatives, conducting organic salts (tetrathiafulvalene-tetracyanoquinodimethane, TTF-TCNQ), hexamineruthenium (III) chloride, quinone compounds, transition-metal complexes, and phenothiazine and phenoxazine compounds, are particularly useful to electrically contact glucose oxidase.

The electrode assembly 108 desirably includes underfill electrodes 120, which are located on one or both surfaces of the substrate 110. It is contemplated that an electrochemical sensor may include other electrodes such as an underfill electrode, hematocrit-detection electrode. As shown in FIGS. 2A-2C, the electrode assembly 108 includes a pair of underfill electrodes 120 that are located on the first and/or second substrate surfaces 112, 114, whereby the pair of underfill electrodes 120 are adjacent located between the sides 113a, 113b of the assembly 108 and the center sections 115a, 115b of the respective electrodes 116, 118.

In particular, as shown in FIG. 2B, underfill electrode 120a is located between the side 113a and the center section 115a, whereas another underfill electrode 120b is located between side 113b and the center section 115a. Regarding the opposing side, as shown in FIG. 2C, underfill electrode 121a is located between the side 113b and the center section 115b, whereas the other underfill electrode 121b is located between side 113a and the center section 115a. It is contemplated in another embodiment that only one underfill electrode 120, instead of a pair, be located on either or both surfaces of the substrate.

Figure 3A:
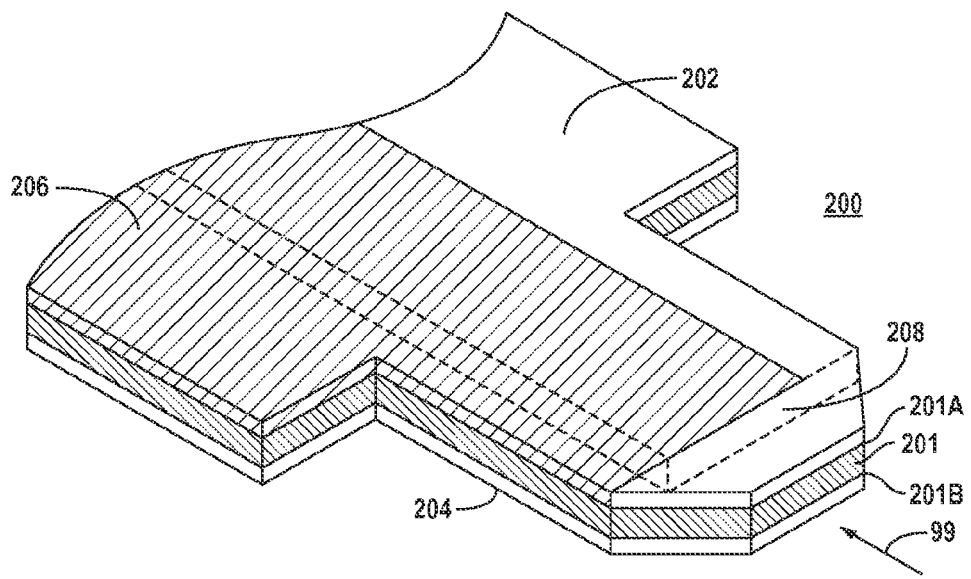
FIG. 3A is a perspective view of an electrode assembly according to another embodiment.
Figure 3B:
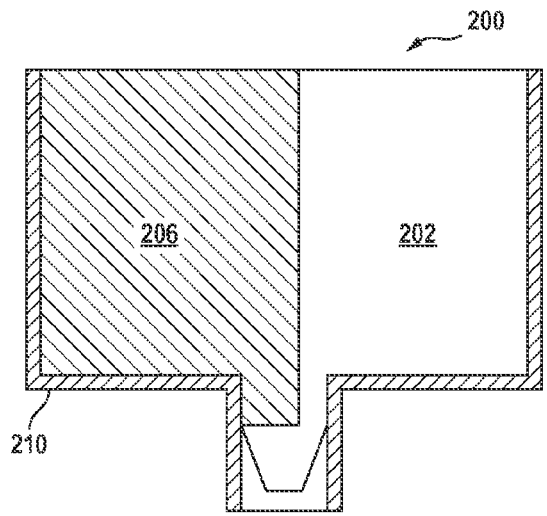
FIG. 3B is a top view of an electrochemical test sensor according to an embodiment.
Figure 3C:
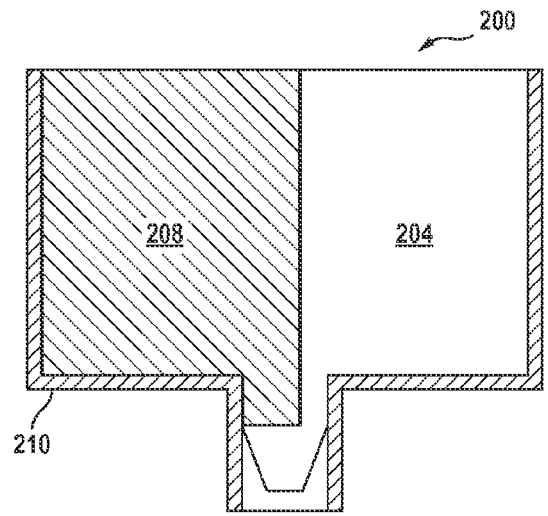
FIG. 3C is a bottom view of an electrochemical test sensor according to an embodiment.

FIGS. 3A-3C illustrate an alternative electrode assembly 200 in accordance with another embodiment. The assembly 200 includes a substrate 201 having a first side 201A and a second side 201B. A working electrode 202 is shown disposed on the first side 201A and a counter electrode 204 are disposed on the opposing second side 201B. Additionally, a first underfill electrode 206 is disposed adjacent to the working electrode 202 on the first side 201A. A second underfill electrode 208 is disposed adjacent to the counter electrode 204 on the second side 201B of the substrate 201.

As shown in the perspective view of FIG. 3A, the working electrode 202 having a generally L-shaped configuration, whereby the underfill electrode 206 is located adjacent to the working electrode 202 and occupies the remainder of the first side 201A of the substrate. In addition, the counter electrode 204 on the second side 201B of the substrate has a generally L-shaped configuration along with the corresponding underfill electrode 208.

In particular, the underfill electrodes 206, 208 on the opposing surfaces of the substrate 201 are inverted with respect to one another. As shown in FIG. 3A, the L-shaped working electrode 202 is located on the right side of the electrode assembly 200 (as viewed from the arrow 99), whereas the L-shaped counter electrode 204 is located on the left side of the electrode assembly 200 (as viewed from the arrow 99).

FIGS. 3B and 3C illustrate the opposing surfaces of the electrode assembly 200 within a housing 210. As shown in FIGS. 3B and 3C, the underfill electrodes 206 (FIG. 3B) and 208 (FIG. 3C) appear on the same side laterally with respect to the corresponding electrode 202, 204. It is contemplated, however, that the underfill electrodes may mirror one another and are not inverted such that they are laterally located in the same area on opposing sides of the substrate.

Figure 4:
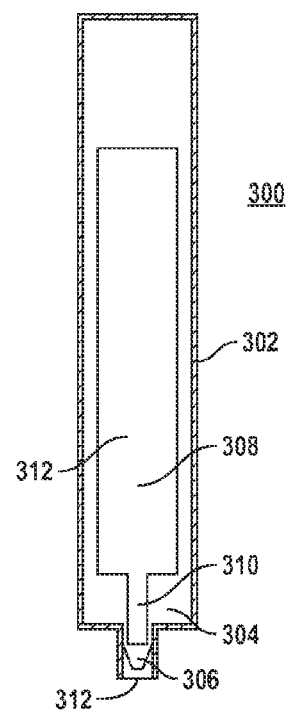
FIG. 4 is a top view of an electrochemical test sensor according to an embodiment.

FIG. 4 illustrates an electrochemical test sensor in accordance with another embodiment. As shown in FIG. 4, the electrochemical test sensor 300 includes a housing 302 with a front opening end 312. An electrode assembly 304 is positioned within the housing 302 and includes a tip 306 proximal to the front opening end 312 of the housing 302.

As shown in FIG. 4, an underfill electrode 308 is located approximately centrally along the surface of the electrode assembly 304. The underfill electrode 308 includes a main body 312 and an extension leg 310 which extends toward the tip 306 of the electrode 304. The extension leg 310 desirably has a width dimension smaller than the main body 312 of the underfill electrode 308. It is contemplated that the other side of the electrode assembly 304 may have a similar configuration to that shown in FIG. 4, although it is not necessary. It should be noted that the above configurations of the underfill electrodes on the electrode assembly are examples and other designs, orientations, layouts and positions are contemplated.

It is contemplated that the sensors may be used to detect more than one analyte using modifications of the embodiments discussed above. In such an embodiment, an additional working electrode would be added to the sensor on an opposing side of the existing working electrode. The reagents to be used on the respective working electrode would be appropriately selected to assist in determining the concentrations of the desired analytes. Thus, two different analyte concentrations may be determined using one sample. In this embodiment, the counter electrode may be used in conjunction with each of the working electrodes. In another embodiment, a separate counter electrode may be formed on an opposing side of the existing counter electrode.

FIG. 5 illustrates a perspective view of the above described sensor configured for use with a lancet mechanism in accordance with an embodiment. As shown in FIG. 5, a sensor-lancet assembly 400 includes the sensor 402 and a lancet mechanism 404 removably coupled to the sensor 402. In particular, the sensor 402 includes the sensor assembly 406 positioned within the housing 408, in which an electrode tip 410 of the sensor assembly 406 is positioned within a lancet interface 412 coupled to the end of the housing 408.

The lancet mechanism 404 includes a lancet adapter 414 and a lancet needle 416 extending from the lancet adapter 414. The lancet adapter 414 holds the lancet needle in place and also interfaces with the lancet interface 412 of the sensor 402. The lancet needle 416 punctures the user's skin to obtain a fluid sample that will be collected. Although not required, the adapter and interfaces may be configured to allow selective removal and replacement of the lancet mechanism from the sensor.

The lancet adapter 414 is desirably configured to be in communication with the lancet needle 416 and the tip 410 of the sensor 402 such that the fluid sample travels from the lancet needle 416 through the lancet adapter 414 to be received at the sensor tip 410. It is desirable that the electrode tip 410 is precisely positioned within the interface 412 to ensure that it receives a predetermined sample volume. It is also contemplated that the sensor may alternatively be incorporated inside the lancet needle in an embodiment. Although one particular type of electrode sensor 400 is shown in FIG. 5, it should be noted that any of the above described sensor embodiments may be used with the lancet device described herein.

FIG. 6 illustrates a schematic of an integrated sensor and lancet mechanism in accordance with another embodiment. As shown in FIG. 6, integrated sensor/lancet 500 has a housing 502 and a sensor 504 located within the housing 502. The housing 502 forms an opening 507. The sensor 504 includes a tapered tip 506 that extends out from the opening 507 and forms a sharp end 508. Thus, the portion of the sensor 500 exposed outside of the housing 502 functions as a lancet needle 510. As shown in FIG. 6, the lancet needle 510 desirably includes a sample transport channel 512 that terminates at an aperture at (or proximal to) the sharp end 508 of the needle 510. The transport channel 512 is configured to be in communication with the tapered tip 506 of the sensor 504 and is desirably treated with a hydrophilic material such that the sample automatically travels upward from the incision site directly to the sensor 504 without the need for any additional components or attachments.

In operation, the integrated sensor/lancet 500 extends toward the user's skin, whereby the needle 510 makes a small incision in the skin. The fluid sample desirably flows upward via the channel 512 to the tapered area 506. It is desirable that the tapered area 506 is precisely positioned within the housing 502 to ensure that it receives a predetermined sample volume. Although one particular type of electrode sensor 504 is shown in FIG. 6, it should be noted that any of the above described sensor embodiments may be used with the lancet assembly described herein.

In another embodiment, the integrated sensor/lancet 500 of FIG. 6 may be modified for use in a continuous glucose-monitoring (CGM) system. In such an embodiment, the integrated sensor/lancet may be simplified by eliminating unnecessary items such as the housing 502, resulting in a system without a sample transport channel 512 being formed. In a continuous glucose monitoring embodiment, the underfill detection electrodes are not necessary. The continuous glucose-monitoring system includes a working electrode on one side and a counter electrode on the opposing side as discussed above. The working electrode in this embodiment may be formed of, for example, platinum or gold and the counter electrode may be formed of, for example, silver/silver chloride. It is contemplated that other materials may be used in forming the electrodes to be used in the glucose-monitoring system. A tapered tip in the continuous glucose-monitoring system would extend out to form a sharp end that assists in inserting the modified integrated sensor/lancet into the skin.

In one or more of the above embodiments, the working electrode desirably has a surface area of approximately 0.6 mm$^2$ or less. It is also desirable for the working electrode to use a sample volume between and including 0.1 and 0.3 μL, and desirably from about 0.15 to about 0.2 μL, although other sample volumes are contemplated. It is contemplated that the sample size may even be smaller such as from about 0.05 to about 0.3 μL, and desirably from about 0.05 to about 0.2 μL.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

What is claimed is:

1. A method for continuously determining the concentration of an analyte in a fluid sample with a test sensor, the method comprising:
   providing an electrochemical test sensor including a housing and an electrode assembly, the housing having a first end and a second opposing end, the housing including an opening at the first end to receive a fluid test sample, the electrode assembly including a solid substrate, a working electrode, a counter electrode and a reagent, the solid substrate having a first surface and an opposing second surface, the working electrode being disposed on the first surface of the solid substrate, the counter electrode being disposed on the second surface of the solid substrate, the electrode assembly being positioned within the housing to define a reaction channel, the electrode assembly extending across a width dimension of an interior of the housing to form a first capillary channel being exposed to the working electrode and a second capillary channel being exposed to the counter electrode;
   providing the fluid sample to the reaction channel such that the fluid sample flows only on the exterior of the solid substrate so as to contact the working and counter electrodes;
   providing an integrated lancet being exposed outside of the opening, the lancet being integrated with the electrochemical test sensor, the integrated lancet including a lancet needle, the lancet needle including a fluid channel therein configured to pass the fluid sample from an incision via capillary action;
   reacting the analyte of the fluid sample with the reagent to generate an electrical signal in the sensor in response to the presence of the analyte in the fluid sample; and
   continuously determining the analyte concentration using the electrical signal.

2. The method of claim 1, wherein the first and second capillary channels are in communication with one another at the reaction channel.

3. The method of claim 1, wherein the electrode assembly includes first and second sides located between first and second surfaces, the first and second sides at one end being tapered toward each other.

4. The method of claim 1, wherein a volume of the fluid sample is from about 0.1 μL to about 0.3 μL.

5. The method of claim 1, wherein a volume of the reaction channel is less than 0.5 μL.

6. The method of claim 1, wherein a volume of the reaction channel is less than 0.3 μL.

7. The method of claim 1, wherein a volume of the reaction channel is from about 0.1 μL to about 0.5 μL.

8. The method of claim 1, wherein the housing at a first end has a circular cross-sectional shape.

9. The method of claim 1, wherein the integrated lancet includes a tapered tip to assist in inserting into the skin.

10. A method for continuously determining the concentration of glucose in a fluid sample with a test sensor, the method comprising:
    providing an electrochemical test sensor including a housing and an electrode assembly, the housing having a first end and a second opposing end, the housing including an opening at the first end to receive a fluid test sample, the electrode assembly including a solid substrate, a working electrode, a counter electrode and a reagent, the solid substrate having a first surface and an opposing second surface, the working electrode being disposed on the first surface of the solid substrate, the counter electrode being disposed on the second surface of the solid substrate, the electrode assembly being positioned within the housing to define a reaction channel, the electrode assembly extending across a width dimension of an interior of the housing to form a first capillary channel being exposed to the working electrode and a second capillary channel being exposed to the counter electrode;
    providing the fluid sample to the reaction channel such that the fluid sample flows only on the exterior of the solid substrate so as to contact the working and counter electrodes;
    providing an integrated lancet being exposed outside of the opening, the lancet being integrated with the electrochemical test sensor, the integrated lancet including a lancet needle, the lancet needle including a fluid channel therein configured to pass the fluid sample from an incision via capillary action;
    reacting the glucose of the fluid sample with the reagent to generate an electrical signal in the sensor in response to the presence of the glucose in the fluid sample; and
    continuously determining the glucose concentration using the electrical signal.

11. The method of claim 10, wherein the first and second capillary channels are in communication with one another at the reaction channel.

12. The method of claim 10, wherein the electrode assembly includes first and second sides located between first and second surfaces, the first and second sides at one end being tapered toward each other.

13. The method of claim 10, wherein a volume of the fluid sample is from about 0.1 μL to about 0.3 μL.

14. The method of claim 10, wherein a volume of the reaction channel is less than 0.5 μL.

15. The method of claim 10, wherein a volume of the reaction channel is less than 0.3 μL.

16. The method of claim 10, wherein a volume of the reaction channel is from about 0.1 μL to about 0.5 μL.

17. The method of claim 10, wherein the housing at a first end has a circular cross-sectional shape.

18. The method of claim 10, wherein the integrated lancet includes a tapered tip to assist in inserting into the skin.

19. A method for continuously determining the concentration of an analyte in a fluid sample with a test sensor, the method comprising:

providing an electrochemical test sensor including a housing and an electrode assembly, the housing having a first end and a second opposing end, the housing including an opening at the first end to receive a fluid test sample, the electrode assembly including a solid substrate, a working electrode, a counter electrode and a reagent, the solid substrate having a first surface and an opposing second surface, the working electrode being disposed on the first surface of the solid substrate, the counter electrode being disposed on the second surface of the solid substrate, the electrode assembly being positioned within the housing to define a reaction channel, the electrode assembly extending across a width dimension of an interior of the housing to form a first capillary channel being exposed to the working electrode and a second capillary channel being exposed to the counter electrode;

providing the fluid sample to the reaction channel such that the fluid sample contacts the working and counter electrodes;

providing an integrated lancet being exposed outside of the opening, the lancet being integrated with the electrochemical test sensor, the integrated lancet including a lancet needle, reacting the analyte of the fluid sample with the reagent to generate an electrical signal in the sensor in response to the presence of the analyte in the fluid sample; and continuously determining the analyte concentration using the electrical signal.

20. The method of claim 19, wherein the analyte is glucose.

21. The method of claim 19, wherein the first and second capillary channels are in communication with one another at the reaction channel.

22. The method of claim 19, wherein the electrode assembly includes first and second sides located between first and second surfaces, the first and second sides at one end being tapered toward each other.

23. The method of claim 19, wherein the housing at a first end has a circular cross-sectional shape.

24. The method of claim 19, wherein the integrated lancet includes a tapered tip to assist in inserting into the skin.

* * * * *

UNITED STATES PATENT AND TRADEMARK OFFICE
CERTIFICATE OF CORRECTION

PATENT NO. : 9,034,172 B2
APPLICATION NO. : 12/877207
DATED : May 19, 2015
INVENTOR(S) : Yuan Wang et al.

Page 1 of 1

It is certified that error appears in the above-identified patent and that said Letters Patent is hereby corrected as shown below:

On the title page item (75), under "Inventors", in Column 1, Line 2, delete "Cortland Manor," and insert -- Cortlandt Manor, --, therefor.

IN THE SPECIFICATION:

In Column 4, Line 18, delete "polysterene," and insert -- polystyrene, --, therefor.

In Column 4, Line 53, delete "hexamineruthenium (III)" and insert -- hexaammineruthenium (III) --, therefor.

In Column 5, Line 16, delete "204 are" and insert -- 204 is --, therefor.

In Column 5, Line 23, delete "202 having" and insert -- 202 has --, therefor.

IN THE CLAIMS:

In Column 8, Line 2, in Claim 1, delete "sensor" and insert -- electrochemical test sensor --, therefor.

In Column 8, Line 55, in Claim 10, delete "sensor" and insert -- electrochemical test sensor --, therefor.

In Column 10, Line 11, in Claim 19, delete "sensor" and insert -- electrochemical test sensor --, therefor.

Signed and Sealed this
Twenty-ninth Day of December, 2015

Michelle K. Lee
*Director of the United States Patent and Trademark Office*